United States Patent [19]

Nakajima et al.

[11] Patent Number: 5,011,590
[45] Date of Patent: Apr. 30, 1991

[54] TEMPERATURE CONTROL DEVICE FOR OXYGEN CONCENTRATION SENSOR

[75] Inventors: Toyohei Nakajima; Toshiyuki Mieno, both of Wako, Japan

[73] Assignee: Honda Giken Kogyo Kabushiki Kaisha, Tokyo, Japan

[21] Appl. No.: 284,284

[22] Filed: Dec. 14, 1988

[30] Foreign Application Priority Data

Dec. 14, 1987 [JP] Japan ................... 62-316569

[51] Int. Cl.$^5$ ................ G01N 27/41; G01N 27/409
[52] U.S. Cl. .................... 204/425; 204/408; 204/412; 204/426
[58] Field of Search ............. 204/15, 421–429; 219/497, 499

[56] References Cited

U.S. PATENT DOCUMENTS

| | | | |
|---|---|---|---|
| 2,897,333 | 7/1959 | McFarlane et al. | 219/497 |
| 4,348,583 | 9/1982 | Bube et al. | 219/499 |
| 4,464,244 | 8/1984 | Uchida et al. | 204/425 |
| 4,500,412 | 2/1985 | Takahashi et al. | 204/429 |
| 4,505,807 | 3/1985 | Yamada | 204/425 |
| 4,510,036 | 4/1985 | Takeuchi et al. | 204/408 |
| 4,611,562 | 9/1986 | Nakano et al. | 204/426 |
| 4,708,777 | 11/1987 | Kuraoka | 204/425 |
| 4,721,084 | 1/1988 | Kawanabe et al. | 204/424 |
| 4,736,091 | 4/1988 | Moe | 219/497 |
| 4,787,966 | 11/1988 | Nakadima et al. | 204/425 |

Primary Examiner—T. Tung
Attorney, Agent, or Firm—Pollock, Vande Sande & Priddy

[57] ABSTRACT

A temperature control device for an oxygen concentration sensor having a solid electrolytic member having oxygen ion-conductivity, a gas diffusion-limiting zone defined by the solid electrolytic member and into which is introduced a gas the concentration of which is to be examined, and a couple of electrodes between which the solid electrolytic member is interposed. Pumping current is supplied to the solid electrolytic member and flows therein between the electrodes to cause an oxygen ion flow in the solid electrolytic member between the electrodes to vary the concentration of oxygen present within the gas diffusion-limiting zone. The pumping current is varied in response to the concentration of oxygen within the gas diffusion-limiting zone, whereby the concentration oxygen in the gas is detected from the pumping current value. The temperature control device comprises a series circuit of an electrically heating element for heating the solid electrolytic member and a switching element, a power supply for supplying a direct current voltage to the series circuit, a current detector for detecting heating current flowing in the heating element, and a driving circuit responsive to the detected heating current for selectively energizing and deenergizing the switching element. A resistance is connected in parallel with the switching element for always allowing the supply of a small amount of current to the heating element irrespective of whether the switching element is energized or deenergized.

2 Claims, 3 Drawing Sheets

FIG. 1
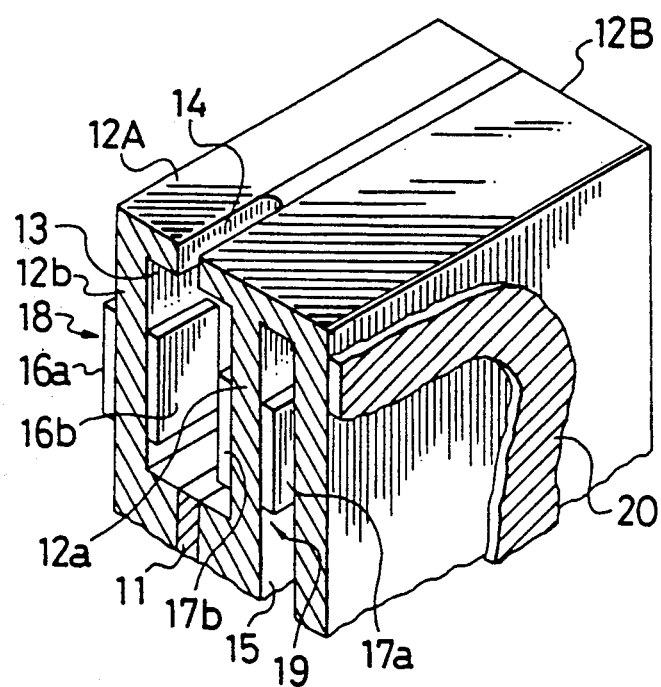
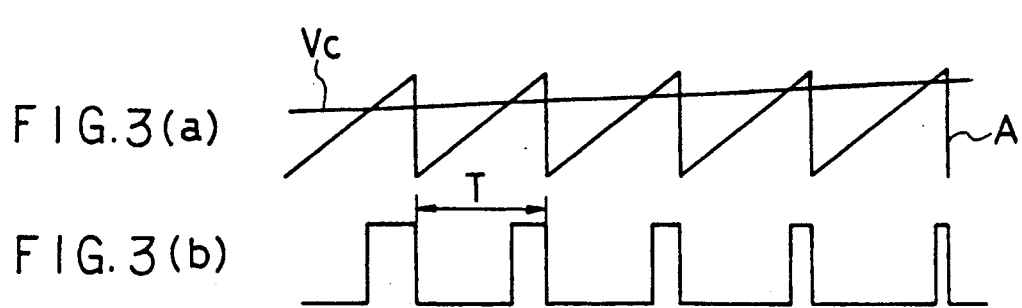
FIG.3(a)
FIG.3(b)

TEMPERATURE CONTROL DEVICE FOR OXYGEN CONCENTRATION SENSOR

BACKGROUND OF THE INVENTION

This invention relates to the temperature control of oxygen concentration sensors, and more particularly to a temperature control device for an oxygen concentration sensor of the type which generates an output proportional to the concentration of oxygen in a gaseous substance such as exhaust gases emitted from an internal combustion engine.

An air-fuel ratio control system for an internal combustion engine is generally employed, which senses the concentration of oxygen in exhaust gases emitted from the engine by means of an oxygen concentration sensor. The control system controls the air-fuel ratio of a mixture supplied to the engine, in a feedback manner responsive to the output signal from the oxygen concentration sensor, to thereby purify the exhaust gases and improve the fuel consumption, etc.

In recent years, a type of oxygen concentration sensor has been developed for use in the air-fuel ratio control system, which generates an output proportional to the concentration of oxygen contained in the exhaust gases. A sensor of this type is disclosed, e.g. in Japanese Provisional Patent Publication (Kokai) No. 59-192955, which comprises an oxygen-pumping element and a cell element, each being composed of a plate-like member formed of a solid electrolytic material having oxygen ion-conductivity, and a couple of electrodes. A gas-staying chamber is provided as a gas diffusion-limiting zone between the oxygen-pumping element and the cell element, with one of the coupled electrodes of each element being attached to one of opposite inner walls of the chamber. A gas to be examined is introduced into the gas-staying chamber through a gas-introducing slit. An air chamber into which the atmosphere is introduced is provided adjacent the cell element, with the other of the coupled electrodes of the cell element facing the interior of the air chamber.

According to the disclosed sensor, when a voltage developed between the two electrodes of the cell element is above a predetermined reference voltage, a voltage corresponding to the difference between them is supplied to the oxygen-pumping element so that oxygen ions move through the oxygen-pumping element toward the electrode located in the gas-staying chamber or gas diffusion-limiting zone. When the voltage between the two electrodes of the cell element is below the predetermined reference value, a voltage corresponding to the difference between them is supplied to the oxygen-pumping element so that oxygen ions move toward the electrode located outside the gas-staying chamber. Thus, electric current flowing between the two electrodes of the oxygen-pumping element, i.e. pumping current, assumes a value proportional to the concentration of oxygen in the gas supplied into the gas-staying chamber or gas diffusion-limiting zone.

If an oxygen concentration sensor of the above described type which provides an output proportional to the oxygen concentration is used in feedback control of the air-fuel ratio in an internal combustion engine, attain an output characteristic proportional to the oxygen concentration, the solid electrolytic members have to be maintained at a temperature e.g. 650° C. or more. This temperature is considerably higher than the temperature of exhaust gases, so as to impart sufficient oxygen ion-conductivity to the elements. To this end, an electrical heating element is arranged for the solid electrolytic members at a suitable portion thereof, for heating the same. The heating element is supplied with heating current from a temperature control device. Only after the solid electrolytic members have been fully heated is the air-fuel ratio feedback control responsive to the sensor output started.

As the above temperature control device, a device is disclosed, e.g. in Japanese Provisional Patent Publication (Kokai) No. 60-48518, which comprises a series circuit composed of an electrical heating element and a switching element which are serially connected to each other. A predetermined direct current voltage is applied to the series circuit and a heating current flowing in the heating element is detected. The switching element is turned on and off by driving pulses with a predetermined pulse repetition period at a duty factor corresponding to the magnitude of the heating current. Thus, the heating current applied to the heating element is controlled to desired values by means of the duty factor control.

In the case where the oxygen concentration sensor is used to detect oxygen concentration in exhaust gases from an internal combustion engine, there is a possibility of overheating the sensor when the engine is operating in a high load condition. If the sensor is kept in such an overheated state for a long time, it can deteriorate. One possible way to solve the problem is to detect the temperature of the heating element from the resistance value of same, and interrupt the supply of heating current to the heating element immediately when the resistance value exceeds a predetermined critical value so as to allow the heating element to be cooled. The resistance value may be detected from the value of heating current or the voltage across the heating element. However, in the case where the heating current is controlled by means of the duty factor control as stated above, it is impossible to detect the resistance value during the off period. Further, the pulse repetition period is very short, e.g. 100 ms, which is inappropriate for quick detection of the resistance value.

SUMMARY OF THE INVENTION

It is the object of the invention to provide a temperature control device for an oxygen concentration sensor, which controls the heating current supplied to the electrically heating element of the sensor by means of duty factor control, and is capable of quickly detecting overheating of the sensor.

To attain the above object, the present invention provides a temperature control device for controlling the temperature of an oxygen concentration sensor. The device has a solid electrolytic member having: oxygen ion-conductivity; a gas diffusion-limiting zone defined by the solid electrolytic member, and into which is introduced a gas the oxygen concentration of which is to be examined; a couple of electrodes between which the solid electrolytic member is interposed means for supplying pumping current to the solid electrolytic member, so that the current flows in the solid electrolytic member, between the electrodes, to cause an oxygen ion flow in the solid electrolytic member, between the electrodes, to vary the concentration of oxygen present within the gas diffusion-limiting zone; and, means responsive to the concentration of oxygen within the gas diffusion-limiting zone for varying the pumping current, whereby the concentration of oxygen in the gas is detected from the value of the pumping current.

The temperature control device according to the invention comprises:

an electrical heating element for heating the solid electrolytic member;

a switching element serially connected to the electrical heating element and forming a series circuit together therewith;

a power supply for supplying a direct current voltage to the series circuit of the electrical heating element and the switching element;

current detecting means for detecting heating current flowing in the electrical heating element;

driving means responsive to the value of the heating current detected by the current detecting means for selectively energizing and deenergizing the switching element; and current supply means for always supplying a small amount of current to the electrical heating element irrespective of whether the switching element is energized or deenergized.

Preferably, the current supply means comprises a resistance connected in parallel with the switching element.

Alternatively, the current supply means may comprise a constant current source connected to the juncture between the electrically heating element and the switching element.

The current supply means is applied to a temperature control device wherein the driving means energizes and deenergizes the switching element by driving pulses with a predetermined pulse repetition period at a duty factor corresponding to the value of the heating current detected by the current detecting means.

Preferably, the small amount of current supplied from the current supply means has such a value as not to substantially cause the electrically heating element to be heated.

The above and other objects, features, and advantages of the invention will be more apparent from the ensuing detailed description taken in conjunction with the accompanying drawings.

BRIEF DESCRIPTION OF THE DRAWINGS

FIG. 1 is a perspective view showing an oxygen concentration-sensing section of an oxygen concentration sensor to which is applied the temperature control device according to the invention;

FIGS. 3a and 3b are timing charts showing waveforms of signals produced in the circuit of FIG. 2.

DETAILED DESCRIPTION

Figure 2:
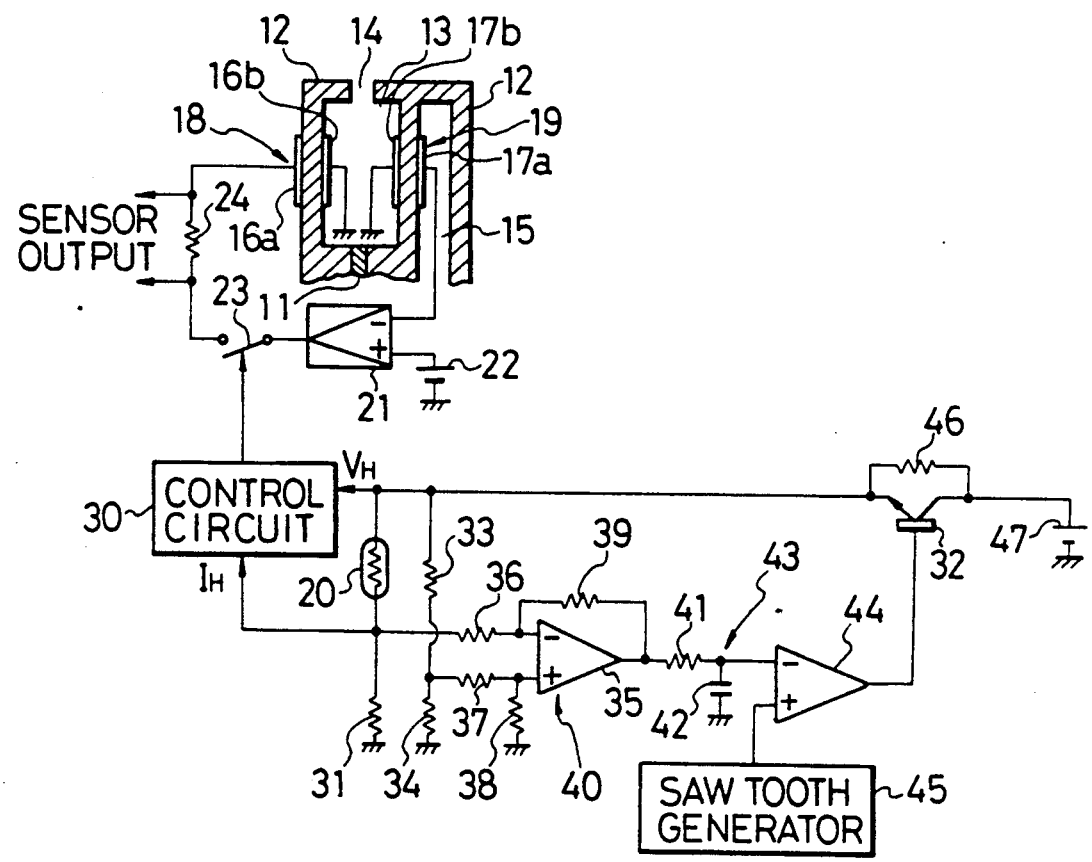
FIG. 2 is a circuit diagram showing an embodiment of the temperature control device according to the invention.

The invention will now be described in detail with reference to the drawings showing embodiments thereof.

Referring first to FIG. 1, there is illustrated an oxygen concentration-sensing section of an oxygen concentration sensor, the temperature of which is to be controlled by a temperature control device according to the invention. The oxygen concentration-sensing section comprises a pair of generally plate-like members 12A and 12B formed of a solid electrolytic material having oxygen ion-conductivity (hereinafter merely called "electrolytic member(s)"), arranged opposite each other, with an insulating layer 11 interposed therebetween. The solid electrolytic material may preferably be zirconium dioxide ($ZrO_2$). And the insulating layer 11 may be formed of alumina. A gas-staying chamber 13 is defined within the electrolytic members 12A, 12B, which serves as a gas diffusion-limiting zone. A gas-introducing slit 14 is defined between upper walls of the electrolytic members 12A, 12B, through which a gaseous substance to be examined, such as exhaust gases from an internal combustion engine, is introduced into the gas-staying chamber 13. If the device is applied to air-fuel ratio feedback control in an internal combustion engine, the slit 14 is disposed such that exhaust gases in an exhaust pipe, not shown, of the engine can be guided into the gas-staying chamber 13 through the slit 14. An air reference chamber 15 which communicates with the atmosphere to be supplied with air is defined within the electrolytic member 12B at a location adjacent the gas-staying chamber 13 by a wall 12a intervening therebetween and separating them from each other. The wall 12a carries on its opposite sides a couple of electrodes 17a and 17b facing the air reference chamber 15 and the gas-staying chamber 13, respectively. The other electrolytic member 12A has a wall 12b defining the other side of the gas-staying chamber 13 and which carries on its opposite sides a couple of electrodes 16a and 16b facing outwardly of the sensor and the gas-staying chamber 13, respectively. The electrodes 17a and 17b, and 16a, 16b may be formed of platinum (Pt). The electrolytic member 12A and the electrodes 16a, 16b cooperatively act as an oxygen-pumping element 18, while the electrolytic element 12B and the electrodes 17a, 17b cooperatively act as a cell element 19.

The above-mentioned insulating layer 11 is interposed between the two elements 18, 19 to electrically insulate them from each other. The electrolytic member 12B has an outer wall defining the air reference chamber 15 and having an outer surface provided with an electrical heating element (hereinafter called "heater") 20 for heating the oxygen-pumping element 18 and the cell element 19. Alternatively, the heater 20 may be arranged at another location, e.g. inside the electrolytic members 12A, 12B.

As shown in FIG. 2, the electrode 16b of the oxygen-pumping element 18 and the electrode 17b of the cell element 17 are grounded. Connected to the electrode 17a of the cell element 19 is a differential amplifier 21 which produces an output voltage corresponding to the difference between a voltage between the electrodes 17a, 17b of the cell element 19 and an output voltage from a reference voltage source 22. The output voltage from the reference voltage source 22 is set at a value corresponding to a stoichiometric mixture ratio of a mixture supplied to the engine at which the conversion efficiency of a three-way catalyst arranged in the exhaust pipe of the engine becomes the maximum, e.g. 0.45 volts. An output terminal of the differential amplifier 21 is connected to the electrode 16a of the oxygen-pumping element 18 by way of a switch 23 having a controllable terminal, and a current-detecting resistance 24. The current-detecting resistance 24 has its opposite ends serving as an output terminal of the oxygen concentration sensor.

A heating current-detecting resistance 31 for detecting heating current or heater current is serially connected at its one end to one end of the heater 20 and grounded at its other end, forming a series circuit together with the heater 20. Connected to the other end of the heater 20 is the emitter of a transistor 32 as a switching element, with its collector connected to a direct current voltage ($V_B$) source 47. The other end of the heater 20 is also connected to a terminal of a control circuit 30 for detecting a voltage $V_H$ applied to the heater 20, while the juncture between the heater 20 and the resistance 31 is connected to another terminal of the control circuit 30 for detecting heater current $I_H$ flowing in the heater 20. The control circuit 30 operates in response to the volta $V_H$ applied to the heater 20 and the heater current $I_H$ to turn the switch 23 on and off. Another series circuit formed of resistances 33 and 34 is connected in parallel with the series circuit of the heater 20 and the resistance 31. The divided voltage at the juncture between the heater 20 and the resistance 31 and that at the juncture between the resistances 33, 34 are supplied to a differential amplifier circuit 40 formed of an operational amplifier 35, and resistances 36-39, which produces an output voltage corresponding to the difference between the two divided voltages. The output voltage from the differential amplifier circuit 40 is supplied to an inverting input terminal of a comparator 44 through an integrating circuit 43 formed of a resistance 41 and a capacitor 42. Connected to a non-inverting input terminal of the comparator 44 is a saw tooth generator 45 which generates a saw tooth wave signal having a predetermined period T (e.g. 100 ms), so that the comparator 44 compares between the saw tooth wave signal and the output voltage from the integrating circuit 43. The output from the comparator 44 is supplied to the base of the transistor 32. A resistance 46 as current supply means is connected between the collector and emitter of the transistor 32.

With the above described arrangement, when the output from the comparator 44 goes high, the transistor 32 is turned on. This causes an output voltage or emitter voltage from the transistor 32 to be applied to the series circuit of the heater 20 and the resistance 31, whereby heater current is created to heat the oxygen-pumping element 18 and the cell element 19. At this time, the voltage across the resistance 31 is supplied as representing the heater current $I_H$ to the inverting input terminal of the differential amplifier circuit 40. At the same time, the emitter voltage from the transistor 32 is also applied to the series circuit of the resistances 33, 34, so that the divided voltage at the juncture between the resistances 33, 34 is applied as a reference voltage $V_{rl}$ to the non-inverting input terminal of the differential amplifier circuit 40. As a result, an output voltage corresponding to the difference between the voltage across the resistance 31 and the reference voltage is applied to the integrating circuit 43. When the comparator 44 produces a low level output, the transistor 32 is turned off. At this time, a small amount of current flows through the resistance 46 and is delivered to the series circuit of the heater 20 and the resistance 31 and the series circuit of the resistances 33, 34. The voltage across the resistance 31 and the reference voltage $V_{rl}$, which correspond to the small amount of current, are supplied to the differential amplifier circuit 40 which in turn generates an output voltage corresponding to the difference between the two input voltages, and applies same to the integrating circuit 43.

As shown in FIG. 3(a), over a time period during which the level of the saw tooth voltage signal A exceeds the output voltage $V_c$ from the integrating circuit 43, the output level from the comparator 44 is high as shown in of FIG. 3(b) so that the transistor 32 is on. The time period during which the transistor 32 is on, falling within the predetermined period T, becomes shorter as the output voltage V from the integrating circuit 43 increases.

For example, as the exhaust gas temperature rises, the resistance of the heater 20 increases correspondingly so that the difference between the voltage across the resistance 31 and the reference voltage $V_{rl}$ increases and hence the time period during which the transistor 32 is on, within the period T, becomes shorter to decrease the average value of the heater current. Consequently, the heater 20 has a decreased temperature and hence a decreased resistance value. Conversely, as the exhaust gas temperature decreases, the resistance value of the heater 20 decreases. Consequently, the difference between the voltage across the resistance 31 and the reference voltage $V_{rl}$ decreases, the output voltage from the integrating circuit 43 lowers, and hence the time period of energization of the transistor 32 becomes longer to increase the average value of the heater current. As a result, the heater 20 has a higher temperature and hence an increased resistance value. As this feedback cycle is repeated, the heater current is controlled by means of duty factor control so that the resistance value of the heater 20 becomes equal to a predetermined value.

The small amount of current flowing through the resistance 46 and to the two series circuits 20, 31; 33, 34 when the output from the comparator 44 is low, i.e. the transistor 32 is off is so small that it does not substantially cause the heater 20 to be heated.

Due to the supply of the small amount of current to the heater 20 during deenergization of the transistor 32, the voltage $V_H$ applied to the heater 20 and the voltage across the resistance 31 representative of the heater current $I_H$, both applied to the control circuit 30, always assume values higher than zero, irrespective of whether the transistor 32 is on or off. The control circuit 30 calculates the resistance value $R_H$ of the heater 20 by dividing the voltage $V_H$ by the heater current $I_H$, and determines whether or not the calculated resistance value $R_H$ is above a first predetermined value $R_{H1}$ and below a second predetermined value $R_{H2}$ ($R_{H1} < R_{H2}$). When $R_{H1} \leq R_H \leq R_{H2}$ is satisfied, the control circuit 30 judges that the temperature of the electrolytic members 12A, 12B is within a range at which the oxygen concentration sensor can provide a desired proportional output characteristic, and then closes the switch 23. The closure of the switch 23 in turn causes pumping current to flow from the differential amplifier 21 to the oxygen-pumping element 18. On the other hand, when $R_H < R_{H1}$ is satisfied, or when $R_H > R_{H2}$ is satisfied, the control circuit 30 judges that the temperature of the electrolytic members 12A, 12B is too low or too high to obtain the desired proportional output characteristic of the oxygen concentration sensor, and then opens the switch 23 to interrupt the supply of the pumping current to the oxygen-pumping element 18.

After the supply of pumping current to the oxygen-pumping element 18 has thus been started through the closed switch 23, when the mixture supplied to the engine, not shown, assumes a lean air-fuel ratio, a voltage $V_s$ developed between the electrodes 17a, 17b of the cell element 19 is lower than the output voltage $V_{r2}$ from the reference voltage source 22, and hence the differential amplifier circuit 21 produces a positive level output. This high level output is supplied to the series circuit of the resistance 24 and the oxygen-pumping element 18. Then, in the element 18, pumping current flows from the electrode 16a to the electrode 16b so that oxygen present within the gas-staying chamber 13 is ionized by the electrode 16b, and the resulting ions move through the element 18 and is emitted as oxygen gas from the other electrode 16a. Thus, oxygen is pumped out of the gas-staying chamber 13.

As oxygen is pumped out of the gas-staying chamber 13, there occurs a difference in oxygen concentration between the exhaust gases within the gas-staying chamber 13 and the air within the air reference chamber 15. The voltage $V_s$ corresponding to the oxygen concentration difference is developed between the electrodes 17a, 17b of the cell element 19, and applied to the inverting input terminal of the differential amplifier 21, which in turn generates an output voltage proportional to the difference between the input voltage $V_s$ and the output voltage $V_{r2}$ of the reference voltage source 22, and hence the pumping current $I_P$ which is proportional to the concentration of oxygen in the exhaust gases is outputted in the form of a voltage across the resistance 24.

When the mixture assumes a rich air-fuel ratio, the voltage $V_s$ exceeds the output voltage $V_{r2}$ from the reference voltage source 22, so that the differential amplifier 21 produces a negative level output. Consequently, the pumping current flowing between the electrodes 16a, 16b of the oxygen-pumping element 18 now flows in the reverse direction to that mentioned before, that is, from the electrode 16b to the electrode 16a so that oxygen outside the oxygen-pumping element 18 is ionized by the electrode 16a, and the ions move in the element 18 and are emitted in the form of an oxygen gas from the electrode 16b into the gas-staying chamber 13. In other words, oxygen is pumped into the gas-staying chamber 13. In this way, the supply of pumping current is controlled so that oxygen is pumped out of or into the gas-staying chamber 13 so as to maintain the oxygen concentration within the gas-staying chamber 13 constant. That is, the value of pumping current $I_P$ varies in proportion to the oxygen concentration in the exhaust gases as the air-fuel ratio of the mixture changes from the lean region to the rich region or vice versa. The air-fuel ratio feedback control is effected in response to the thus varying pumping current $I_P$.

Figure 4:
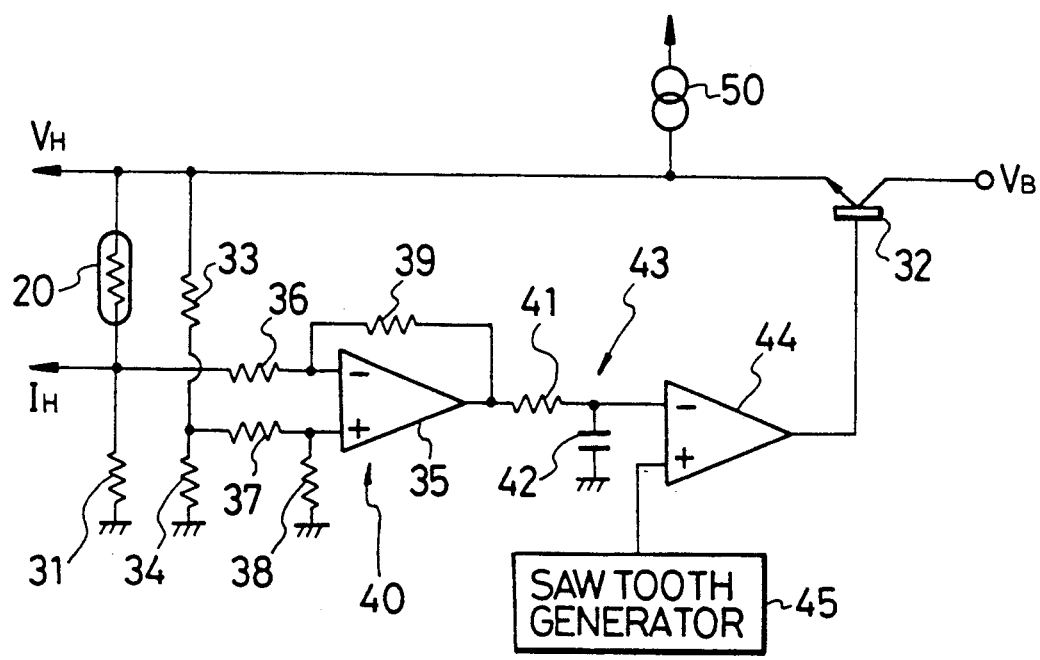
FIG. 4 is a circuit diagram showing another embodiment of the invention.

In the foregoing embodiment the current supply means for supplying a small current level comprises the resistance 46 connected between the collector and emitter of the transistor 32. This is not limitative, but alternatively it may comprise a constant-current source 50 connected to the juncture between the emitter of the transistor 32 and the heater 20, as shown in FIG. 4.

Further, a microcomputer may be used in which the voltage $V_H$ applied to the heater 20 and the heater current $I_H$ are subjected to analog-to-digital (A/D) calculated resistance value $R_H$ and a predetermined reference value.

As described above, since the temperature control device of the invention is provided with the current supply means to supply a small amount of current to the heater to which is serially connected the switching element, it is possible to detect the heater current value even during deenergization of the switching element. Therefore, the resistance value of the heater can be detected from the heater current value all the time during the feedback control, whereby the supply of the pumping current to the oxygen-pumping element and the interruption of same can be determined even during deenergization of the switching element. Thus, deterioration of the oxygen concentration sensor can be positively prevented.

What is claimed is:

1. In an oxygen concentration sensor having first and second solid oxygen ion conductive electrolytic members insulated from each other, a gas diffusion-limiting zone defined by said first and second solid electrolytic members and into which is introduced a gas in which the concentration of oxygen is to be examined, a first pair of electrodes on opposite sides of said first solid electrolytic member, a second pair of electrodes on opposite sides of said second electrolytic member, and means for supplying pumping current to said first solid electrolytic member in response to a voltage generated across said second pair of electrodes so that said current flows in said first solid electrolytic member between said first pair of electrodes to cause an oxygen ion flow in said first solid electrolytic member between said first pair of electrodes, whereby the concentration of oxygen present within said gas diffusion-limiting zone varies, and said voltage is responsive to the concentration of oxygen within said gas diffusion-limiting zone for varying said pumping current, whereby the concentration of oxygen in said gas is detected from the value of said pumping current, a temperature control device for controlling the temperature of said oxygen concentration sensor comprising:

an electrical heating element for heating said first and second solid electrolytic members;

a switching element serially connected to said electrical heating element and forming a series circuit together therewith;

a power supply for supplying a direct current voltage to said electrical heating element and said switching element;

current detecting means for constantly detecting heating current flowing in said electrical heating element;

driving means for selectively energizing said switching element with pulses of a predetermined repetition period having a duty factor corresponding to the value of said heating current detected by the current detecting means for selectively energizing and deenergizing said switching element; and, a resistance connected between input and output terminals of said switching element for constantly supplying a small amount of current to said electrical heating element for detecting the resistance value of said electrical heating element irrespective of whether said switching element is energized or deenergized.

2. A sensor as claimed in claim 1, wherein said small amount of current supplied from said resistance has such a value as not to substantially cause said electrically heating element to be heated.

* * * * *